United States Patent
Narendranath et al.

(10) Patent No.: US 10,190,086 B2
(45) Date of Patent: Jan. 29, 2019

(54) METHODS OF PITCHING YEAST FOR FERMENTATION, AND RELATED METHODS OF FERMENTATION AND SYSTEMS

(71) Applicant: POET Research, Inc., Sioux Falls, SD (US)

(72) Inventors: Neelakantam V. Narendranath, Sioux Falls, SD (US); Stephen M. Lewis, Sioux Falls, SD (US); Neil D. Anderson, Sioux Falls, SD (US)

(73) Assignee: POET Research, Inc., Sioux Falls, SD (US)

( * ) Notice: Subject to any disclaimer, the term of this patent is extended or adjusted under 35 U.S.C. 154(b) by 0 days.

(21) Appl. No.: 14/741,885

(22) Filed: Jun. 17, 2015

(65) Prior Publication Data
US 2015/0368679 A1   Dec. 24, 2015

Related U.S. Application Data

(60) Provisional application No. 62/016,481, filed on Jun. 24, 2014.

(51) Int. Cl.
| | | |
|---|---|---|
| C12P 7/56 | (2006.01) | |
| C12M 1/00 | (2006.01) | |
| C12N 1/16 | (2006.01) | |
| C12N 1/22 | (2006.01) | |
| C12P 7/14 | (2006.01) | |

(52) U.S. Cl.
CPC ............ *C12M 29/00* (2013.01); *C12M 23/58* (2013.01); *C12N 1/16* (2013.01); *C12N 1/22* (2013.01); *C12P 7/14* (2013.01)

(58) Field of Classification Search
None
See application file for complete search history.

(56) References Cited

U.S. PATENT DOCUMENTS

| | | | | |
|---|---|---|---|---|
| 4,978,618 A | * | 12/1990 | Kalina | .............. C12P 7/14 435/162 |
| 5,424,417 A | | 6/1995 | Torget et al. | |
| 6,022,419 A | | 8/2000 | Torget et al. | |
| 7,622,284 B2 | | 11/2009 | Op Den Camp et al. | |
| 7,842,484 B2 | | 11/2010 | Lewis | |
| 8,450,094 B1 | | 5/2013 | Narendranath et al. | |
| 8,815,552 B2 | | 8/2014 | Narendranath et al. | |
| 9,034,631 B2 | | 5/2015 | Narendranath et al. | |
| 2003/0153059 A1 | | 8/2003 | Pilkington et al. | |
| 2014/0065700 A1 | | 3/2014 | Narendranath et al. | |
| 2014/0273166 A1 | | 9/2014 | Narendranath | |
| 2015/0072390 A1 | | 3/2015 | Narendranath et al. | |

FOREIGN PATENT DOCUMENTS

| | | | |
|---|---|---|---|
| EP | 0 277 340 | 8/1988 | |
| WO | WO 2011/159915 | 12/2011 | |
| WO | WO 2012/078885 | * 6/2012 | .............. C12Q 1/44 |
| WO | WO 2012/125739 | 9/2012 | |

OTHER PUBLICATIONS

Smith, Making a Yeast Starter for your Home Brew Beer, BeerSmith Home Brewing Blog, Apr. 1, 2008, Available Online at: beersmith.com/blog/2008/04/01/making-a-yeast-starter-for-your-home-brew-beer/.*

White Labs, Yeast Bank, Accessed Oct. 11, 2016, Online at: www.whitelabs.com/yeast-bank?keywords=&flocculation=0&type=yeasts&temp_from=1&temp_to=100&atten_from=1&atten_to=100&tolerance=453&drink_type=0&yeast_type=0&op=Search&form_build_id=form-JtfdltZfwKF-eNDxee7a9K_5Mt_RFQdYV8H1Zdw OyeE&form_id=whitelabs_yeast_yeast_bank_form.*

King Arthur Flour, Flourish, by Hamel, Maintaining Your Sourdough Starter: Food, Water, and Time, Available Apr. 8, 2012, Online at: blog.kingarthurflour.com /2012/04/08/maintaining-your-sourdough-starter-food-water-and-time/.*

King Arthur Flour, Flourish, by Hamel, How to Make Your Own Sourdough Starter: The Path to Great Bread, Available Apr. 5, 2012, Online at: blog.kingarthurflour.com/ 2012/04/05/ creating-your-own-sourdough-starter-the-path-to-great-bread/.*

Logan et al., Ethanol Content of Various Foods and Soft Drinks and their Potential for Interference with a Breath-Alcohol Test, Journal of Analytical Toxicology, vol. 22, May/Jun. 1998.*

Clawhammer Supply, Corn Whiskey Recipe, Jan. 10, 2014, Available Online at: www.clawhammersupply.com/blogs/moonshine-still-blog/11454449-corn-whiskey-recipe.*

MikeinRH, Splitting the Yeast Starter, BeerSmith Home Brewing Forum, Jun. 4, 2012, Available online at: www.beersmith.com/forum/index.php?topic=7147.0.*

Astor Center, Demystifying Distilled Craft Beer, Tasting Notes from Astor Wines & Spirits, Dec. 5, 2012, Available Online at: tastingnotesnyc.com/2012/12/05/demystifying-distilled-craft-beer/.*

Dictionary.com, Must, Accessed May 23, 2017, Online at: www.dictionary.com/browse/must.*

Ariyajarearnwong, P. et al., "Repeated-batch ethanol fermentation from sweet sorghum juice by free cells of *Saccharomyces cerevisiae* NP 01", African Journal of Biotechnology 10(63) (2011); p. 13909-13918.

Benjaphokee, S. et al., "Highly efficient bioethanol production by a *Saccharomyces cerevisiae* strain with multiple stress tolerance to high temperature, acid and ethanol", New Biotechnology 29(3) (2012); p. 379-386.

(Continued)

*Primary Examiner* — Jennifer M. H. Tichy
(74) *Attorney, Agent, or Firm* — Kagan Binder, PLLC (57) ABSTRACT

The present invention relates to methods and systems of pitching yeast to fermentation reactors. More particularly, the present invention involves pitching yeast from one fermentation tank to at least one additional fermentation tank. Advantageously, yeast can be continuously pitched from fermentor to fermentor for as long as practically desirable.

16 Claims, 10 Drawing Sheets

(56) References Cited

OTHER PUBLICATIONS

Choi, G. et al., "Simultaneous saccharification and fermentation of sludge-containing cassava mash for batch and repeated batch production of bioethanol by *Saccharomyces cerevisiae* CHFY0321", J Chem Technol Biotechnol 84 (2009); p. 547-553.

* cited by examiner

METHODS OF PITCHING YEAST FOR FERMENTATION, AND RELATED METHODS OF FERMENTATION AND SYSTEMS

RELATED APPLICATION

The present non-provisional Application claims the benefit of commonly owned provisional Application having Ser. No. 62/016,481, filed on Jun. 24, 2014, which provisional Application is incorporated herein by reference in its entirety.

FIELD OF INVENTION

The present invention relates to yeast fermentation to produce an alcohol. More particularly, the invention relates to methods and systems of pitching yeast to fermentation reactors.

BACKGROUND OF INVENTION

Organisms that can convert one or more monosaccharides into one or more biochemicals such as biofuels are well known. For example, both genetically modified (referred to as GM) yeast and non-genetically modified (referred to as non-GM) yeast are well known organisms that can convert sugars into alcohols such as ethanol and butanol via fermentation.

Yeast can be conditioned under conditions similar to those used during fermentation so as to, e.g., help the yeast be more effective in producing one or more bioproducts such as ethanol. Oftentimes, conditioning is performed in a propagation system which is typically much smaller in volumetric size as compared to a fermentation system. The conditioned yeast can then be "pitched" (i.e., transferred) from a dedicated conditioning and/or propagating tank to a separate fermentation reactor (i.e., a fermentor). Propagation and conditioning tanks can be a source of bacterial contamination which can impact the performance of yeast during fermentation in a fermentation reactor to an undue degree (e.g., due to bacteria producing undue amounts of lactic acid).

An alternative to pitching yeast from a propagation tank and/or conditioning tank to a fermentation tank includes what is often referred to as "dry-batching." Dry-batching involves directly pitching yeast into a single fermentation tank so as to eliminate propagation and/or conditioning tanks. For example, dry-batching can include directly pitching yeast into each batch fermentation tank of a fermentation system. Such dry-batching techniques can be very expensive due to the amount of fresh yeast pitched directly into each batch fermentation tank.

There is a continuing need to discover improved methods of pitching yeast into a fermentation system (e.g., multiple batch fermentation vessels) in a manner that avoids undue bacterial contamination and/or reduces the amount and cost of yeast.

SUMMARY OF INVENTION

The present invention involves pitching yeast from one fermentation tank to at least one additional fermentation tank. Advantageously, yeast can be continuously pitched from fermentor to fermentor for as long as practically desirable. Dry-batching into each individual fermentor is not necessary which can help save on the cost of yeast. If desired, yeast can be provided to the first fermentation tank from a separate yeast propagation and/or a yeast conditioning tank. However, such a separate yeast propagation and/or yeast conditioning tank is not necessary. Yeast can be provided to the first fermentation tank via dry-batching. Then, yeast can be pitched from the first fermentation tank to a second fermentation tank; from the second fermentation tank to a third fermentation tank; and so on. Advantageously, because a separate yeast propagation and/or a yeast conditioning tank can be omitted if desired, bacterial contamination can be better managed.

According to one aspect of the present invention, a method of pitching yeast for fermentation includes:
providing a first aqueous composition in a first fermentation reactor, wherein the aqueous composition includes:
  yeast;
  a slurry including water and a processed plant material including an amount of at least one monosaccharide;
removing a volume of the first aqueous composition from the first fermentation reactor; and
providing the removed volume of the first aqueous composition to a second fermentation reactor.

According to another aspect of the present invention, a fermentation system for pitching yeast among two or more fermentation reactors includes:
  a source of yeast;
  a source of a slurry, wherein the slurry includes water and a processed plant material including an amount of at least one monosaccharide;
  a first fermentation reactor, wherein the source of yeast and the source of the slurry are each in fluid communication with the first fermentation reactor so that the yeast and slurry can be added to the first fermentation reactor to form a first aqueous composition;
  a second fermentation reactor in fluid communication with the first fermentation reactor so that a volume of the first aqueous composition from the first fermentation reactor can be transferred to the second fermentation reactor to form at least a portion of a second aqueous composition, wherein the source of the slurry is in fluid communication with the second fermentation reactor so that the slurry can be added to the second fermentation reactor and combined with the volume of the first aqueous composition to form the second aqueous composition.

According to another aspect of the present invention, a fermentation system for pitching yeast among two or more fermentation reactors includes:
  a source of yeast;
  a source of a slurry, wherein the slurry includes water and a processed plant material comprising an amount of at least one monosaccharide;
  a first reactor, wherein the source of yeast and the source of the slurry are each in fluid communication with the first reactor so that the yeast and slurry can be added to the first reactor to form a first aqueous composition, wherein the first reactor includes a yeast conditioning reactor or an aerobic yeast propagation reactor;
  a second reactor in fluid communication with the first reactor so that a volume of the first aqueous composition from the first reactor can be transferred to the second reactor to form at least a portion of a second aqueous composition, wherein the second reactor includes a fermentation reactor, wherein the source of the slurry is in fluid communication with the second reactor so that the slurry can be added to the second reactor and combined with the volume of the first aqueous composition to form the second aqueous composition; and a third reactor in fluid communication with the second reactor so that a volume of the second aqueous composition from the second reactor can be transferred to the third reactor to form at least a portion of a third aqueous composition, wherein the third reactor comprises a fermentation reactor, wherein the source of the slurry is in fluid communication with the third reactor so that the slurry can be added to the third reactor and combined with the volume of the second aqueous composition to form the third aqueous composition.

DETAILED DESCRIPTION

The present invention relates to yeast fermentation to produce an alcohol such as ethanol. More particularly, the invention relates to methods and systems of pitching yeast to fermentation reactors (i.e., "fermentors").

An initial step in fermentation involves "pitching" yeast to a fermentation reactor so that the yeast can ferment sugar into alcohol. Pitching yeast means providing an amount of yeast to a fermentation reactor, where the amount of yeast serves as an inoculum in a fermentable composition so that the yeast can ferment sugar into alcohol.

Any of a variety of yeasts, alone or in combination, can be employed as the yeast in a process as described herein. Such yeasts include wild yeast as well as genetically modified yeast. Suitable yeasts include any of a variety of commercially available yeasts, such as commercial strains of *Saccharomyces cerevisiae* available under the trade names, e.g., Ethanol Red® from LeSaffre or TransFerm® from Mascoma Corporation. Exemplary yeast strains can ferment xylose and/or glucose into an alcohol such as ethanol. For example, a useful strain of yeast includes *Saccharomyces cerevisiae* yeast altered to convert (i.e., ferment) xylose and glucose to ethanol (i.e., a genetically modified yeast derived from an organism as described in U.S. Pat. No. 7,622,284). As another example, a useful strain of yeast includes *Saccharomyces cerevisiae* yeast altered (i.e., genetically modified) to convert (i.e., ferment) xylose, arabinose, and glucose to ethanol.

Useful types of yeast can be introduced (i.e., pitched) into a fermentation reactor in any useful form, e.g., as active dry yeast, yeast cream, and combinations thereof.

Yeast can be loaded into a fermentation reactor in any desired amount, e.g., in an amount that can produce a desired amount of an alcohol. Yeast loading can be described in terms of the unit quantity "grams/liter" or "g/L," which means grams of yeast per liter of fermentation medium that the yeast is to be suspended in. A fermentation medium can include an aqueous composition having at least one monosaccharide and, optionally one or more additional components useful in fermentation (e.g., yeast nutrients, bactericides, acids, bases, combinations of these, and the like). For example, a fermentation medium can include a slurry such as slurry 115 described below (e.g., corn mash and one or more optional additives (e.g., urea, bactericide, and one or more enzymes that can convert a polysaccharide to monosaccharides). In some embodiments, yeast can be pitched to a fermentation reactor in amount of at least 0.01 g/L, at least 0.1 g/L, at least 1.0 g/L, or even at least 5.0 g/L. In some embodiments, yeast can be pitched to a fermentation reactor in an amount in the range from 0.1 to 20 g/L, 0.1 to 10 g/L, or even 0.1 to 5 g/L.

The present invention involves pitching yeast from one fermentation tank to at least one additional fermentation tank. Advantageously, yeast can be continuously pitched from fermentor to fermentor for as long as practically desirable. For example, yeast can be pitched in such a continuous serial manner among at least two fermentation tanks, at least three fermentation tanks, at least four fermentation tanks, at least five fermentation tanks, at least seven fermentation tanks, or even at least fifteen fermentation tanks. In some embodiments, pitching yeast according to the present invention includes pitching yeast among a plurality of fermentation tanks that are physically coupled in series so that yeast can be pitched serially from, e.g., a first fermentation tank to a second fermentation tank, then from the second fermentation tank to a third fermentation tank, then from the third fermentation tank to a fourth fermentation tank, etc.

The yeast that is provided (i.e., pitched) to the first fermentation tank can be "dry-batched" (e.g., described below in connection with FIG. 1), provided from a yeast conditioning and/or aerobic yeast propagation tank (e.g., described below in connection with FIG. 2), or a combination thereof.

In some embodiments, a conventional aerated yeast propagation reactor and a conventional yeast conditioning reactor can be omitted. Instead, yeast can be provided directly (i.e., "dry-batched") to a first fermentation tank before pitching an amount of yeast to a second fermentation tank. As used herein, "dry-batching" means adding a yeast ingredient directly to a fermentation tank without first combining the yeast with a conditioning medium and/or propagation medium in a tank separate from the fermentation tank. An exemplary yeast ingredient for dry-batching includes active dry yeast, yeast cream, and combinations thereof.

Figure 1:
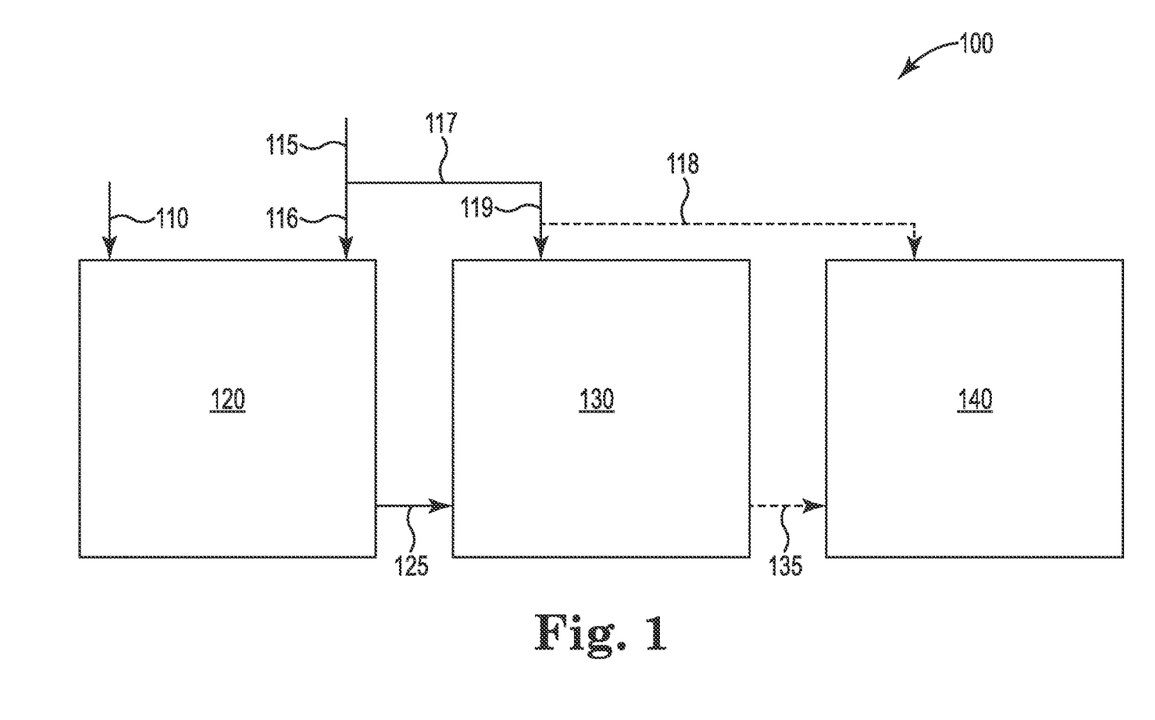
FIG. 1 shows a flow diagram of an exemplary fermentation system according to the present invention for pitching yeast from one fermentation reactor to another fermentation reactor.

FIG. 1 shows a schematic drawing illustrating an exemplary embodiment of a method of pitching yeast for fermentation according to the present invention. As shown, a source of a slurry 115 is in fluid communication with fermentation tank 120 via line 116 so that tank 120 can be filled with the slurry to a desirable level for fermentation.

Slurry 115 can be any fermentable medium for a yeast. For example, slurry 115 can include an aqueous composition having water and a processed plant material. The processed plant material includes an amount of at least one monosaccharide that the yeast can use to convert into an alcohol. Such monosaccharides are derived from polysaccharides present in raw plant material. Further, in addition to including one or more monosaccharides, a processed plant material can also include one or more polysaccharides and/or one or more oligosaccharides. Exemplary monosaccharides include five carbon sugars such as xylose and six carbon sugars such as glucose. Exemplary polysaccharides include cellulose, hemicellulose, and starch that can then be broken down into oligosaccharides and further down to monosaccharides that yeast can use to generate alcohol via fermentation.

Processed plant material can be derived from all or part of any plant. For example, processed plant material can be derived from one or more grains and/or one or more lignocellulosic substrates and/or starchy root crops, tubers, or roots such as sweet potato and cassava. Suitable grains include maize (corn, e.g., ground whole corn), sorghum (milo), barley, wheat, rye, rice, and millet. Suitable lignocellulosic substrates include hardwoods, grasses, softwood, waste paper and pulp, municipal wastes, agricultural wastes such as straws, corn cobs, corn stover, and mixtures thereof. Lignocellulosic feedstock is well known and includes cellulose, hemicellulose and lignin.

A plant can be processed by any technique so as to provide a processed plant material that includes an amount of at least one monosaccharide. For example, corn grain can be ground (e.g., via dry grinding) into corn flour and then mixed with water and/or backset to make a slurry. The slurry can be combined with one or more enzymes that can break down starch in the corn flour into glucose. One preferred technique for processing corn grain to be used in fermentation avoids "cooking" and is described in U.S. Pat. No. 7,842,484 (Lewis), wherein said patent is incorporated herein by reference for all purposes.

Another technique for processing a plant to provide a processed plant material that includes an amount of at least one monosaccharide includes hydrolyzing a lignocellulosic substrate to provide a solid component including glucan and lignin and a liquid component including a monosaccharide such as xylose and/or glucose. In some embodiments, the solid component can be separated from the liquid component so that the liquid component can be used to form at least a portion of the processed plant material for fermentation as described herein. Hydrolyzing lignocellulosic substrates to provide, e.g., xylose and/or glucose is well-known and is described in, e.g., U.S. Pat. No. 5,424,417 (Torget et al.); U.S. Pat. No. 6,022,419 (Torget et al.); and U.S. Pat. No. 8,450,094 (Narendranath et al.), wherein the entireties of said patent documents are incorporated herein by reference for all purposes.

Optionally, slurry 115 can include one or more additional components. For example, slurry 115 can include added nutrients (e.g., yeast micronutrients), urea, bacteriophages, antibiotics, salts, added enzymes, and the like. Nutrients can be derived from stillage that is added to slurry 115. Stillage is obtained from distillation of fermented beer and is recovered as the bottoms portion of a distillation unit. Stillage can be separated into components including a thin stillage component (also referred to as "backset") and a wet distillers grains component. Suitable salts can include zinc or magnesium salts, such as zinc sulfate, magnesium sulfate, and the like. Suitable added enzymes include those added to conventional processes, such as protease, phytase, cellulase, hemicellulase, exo- and endo-glucanase, xylanase, and the like.

As shown, yeast source 110 is also in fluid communication with fermentation tank 120 so that yeast can be combined with slurry 115 and form a fermentable aqueous composition so that yeast can convert sugar into an alcohol.

One aspect of the present invention involves removing a volume of the aqueous composition from the first fermentation reactor 120 and pitching it to a second fermentation reactor 130 via line 125.

The volume of the aqueous composition that is pitched from reactor 120 to reactor 130 can serve as an inoculum for fermentation in reactor 130. In some embodiments, the volume of the aqueous composition that is pitched from reactor 120 to reactor 130 includes a volume similar to or the same as the volume provided by a conventional propagation or conditioning reactor. Exemplary volumes of aqueous compositions that can be pitched from one fermentation reactor to another fermentation reactor include volumes from 5,000 US gallons to less than 100,000 US gallons. In some embodiments, the volume of aqueous compositions that can be pitched from one fermentation reactor to another fermentation reactor includes a volume from 10,000 US gallons to 40,000 US gallons (e.g., 20,000 US gallons).

The volume of the aqueous composition that is pitched from reactor 120 to reactor 130 can be pitched when reactor 120 is full or as reactor 120 is filling with slurry 115 and yeast 110. Oftentimes, the volume of the first aqueous composition is removed from the first fermentation reactor 120 when the first fermentation reactor 120 is substantially filled with the aqueous composition that includes slurry 115 and yeast 110.

In some embodiments, the aqueous composition (slurry 115 and yeast 110) in fermentation tank 120 is exposed to conditions in tank 120 for a period of time to grow and adapt the yeast before removing a volume of the aqueous composition from tank 120 and pitching the aqueous composition to fermentation tank 130 via line 125.

Adapting (also referred to herein as "conditioning") yeast means exposing yeast to conditions that are similar to or the same as conditions used for fermentation so as to help the yeast acclimate when the yeast is exposed to a fermentation environment such as in a fermentation reactor.

Conditions for conditioning an aqueous composition that includes yeast include at least one or more of time, temperature, pH, and stirring. In exemplary embodiments, yeast can be conditioned in fermentation tank 120 at a temperature in the range from 15° C. to 50° C., preferably from 20° C. to 40° C., and even more preferably from 25° C. to 40° C.

In exemplary embodiments, yeast can be conditioned in fermentation tank 120 for a period of time of at least 5 hours, at least 8 hours, or even at least 24 hours. For example, from 5 hours to 100 hours, from 16 hours to 90 hours, from 5 to 30 hours, or even from 24 to 72 hours.

The aqueous composition in tank 120 including yeast 110 and slurry 115 can have a pH that promotes conditioning the yeast. In exemplary embodiments, the aqueous composition in tank 120 including yeast 110 and slurry 115 can have a pH of about 6 or less, a pH of about 3 to about 6, about 3.5 to about 6, about 4 to about 5, about 4 to about 4.5, or about 4.5 to about 5. The initial pH of the aqueous composition can be adjusted by addition of, for example, ammonia, potassium hydroxide, sulfuric acid, phosphoric acid, process waters (e.g., stillage (e.g., thin stillage (backset)), evaporator condensate (distillate), side stripper bottoms, and the like), and the like. Further, the pH can be selected so as to promote yeast growth while inhibiting the growth of contaminant bacterial strains such as lactic and acetic acid bacteria. For example, a pH in the range of 3.5 to 4.0 may facilitate growth of yeast while inhibiting the growth and function of contaminating bacteria.

In some embodiments, it may be desirable to stir the aqueous composition in fermentation tank 120 during at least the conditioning period so as to keep the components well mixed in the aqueous composition (i.e., the yeast 110 and slurry 115).

Depending on the conditions selected for conditioning (e.g., time, etc.), the aqueous composition in tank 120 may or may not ferment and convert sugar to alcohol before removing a volume of the aqueous composition from the first fermentation reactor 120 and pitching it to a second fermentation reactor 130 via line 125.

In some embodiments, the aqueous composition in tank 120 may be subjected to conditions so as to produce an amount of alcohol such that the volume of the aqueous composition from the first fermentation reactor 120 is not bactericidal. For example, the aqueous composition in the first fermentation reactor 120 may include an alcohol at a concentration of less than 15 percent by volume when the volume of the aqueous composition is removed from the first fermentation reactor 120 and pitched to second fermentation reactor 130 via line 125.

In some other embodiments, the aqueous composition in tank 120 may be subjected to conditions so as to produce an amount of alcohol such that the volume of the aqueous composition from the first fermentation reactor 120 is bactericidal. For example, the aqueous composition in the first fermentation reactor 120 may include an alcohol at a concentration of at least 15 percent (or even at least 19 percent) by volume when the volume of the aqueous composition is removed from the first fermentation reactor 120 and pitched to second fermentation reactor 130 via line 125.

After yeast is pitched to the second fermentation reactor 130, reactor 130 can be filled with slurry 115 via lines 117 and 119 and in a manner similar to filling fermentation reactor 120 with slurry 115.

Optionally, as indicated by the dotted lines in FIG. 1, yeast can be pitched from second fermentation reactor 130 to third fermentation reactor 140 in a manner similar to that described above with respect to pitching yeast from first fermentation reactor 120 to second fermentation reactor 130. For example, a volume of the aqueous composition from the second fermentation reactor 130 can be removed and pitched to third fermentation reactor 140 via line 135. The volume of the aqueous composition that is pitched from reactor 130 to reactor 140 can serve as an inoculum for fermentation in reactor 140. After yeast is pitched to the third fermentation reactor 140, reactor 140 can be filled with slurry 115 via lines 117 and 118 and in a manner similar to filling fermentation reactor 120 with slurry 115.

Fermentation reactors useful in the present invention are well known and include a wide variety of volumetric capacities. Exemplary volumetric capacities for fermentation reactors such as reactors 120, 130, and 140 include from 100,000 US gallons to 750,000 US gallons (e.g., 550,000 US gallons), from 200,000 US gallons to 750,000 US gallons, and even from 300,000 US gallons to 750,000 US gallons.

Figure 2:
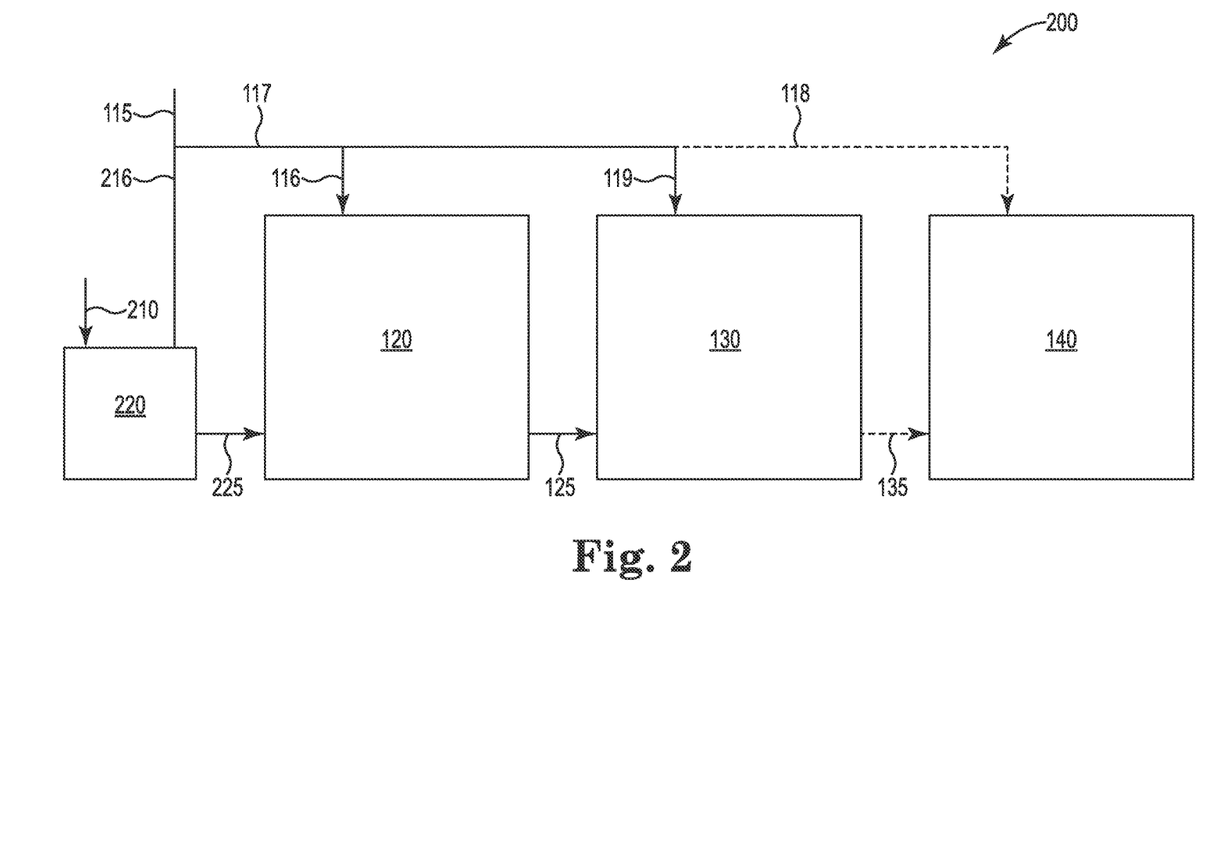
FIG. 2 shows a flow diagram of another exemplary fermentation system according to the present invention for pitching yeast from one fermentation reactor to another fermentation reactor.

As mentioned above, in some embodiments, a conventional aerated yeast propagation reactor or a conventional yeast conditioning reactor can be used to pitch yeast to the first fermentation reactor 120 discussed above instead of or in addition to dry-batching yeast to first fermentation reactor 120. FIG. 2 shows a schematic drawing illustrating an exemplary embodiment of such a method that uses a conventional aerated yeast propagation reactor or a conventional yeast conditioning reactor to pitch yeast to a fermentation reactor, where the fermentation reactor is then used to pitch yeast to at least one additional fermentation reactor. FIG. 2 includes reference characters that are also included in FIG. 1 to represent substantially the same features discussed above with respect to FIG. 1. Unless otherwise noted below, a discussion of said repeated reference characters is not included with respect to the discussion below of FIG. 2.

For purposes of discussion of the embodiment described in FIG. 2, tank 220 represents a conventional vessel for aerobically propagating yeast and/or conditioning yeast (discussed above) for fermentation. Such vessels are well known and are separate from a fermentation tank so that they can be dedicated to the purpose of propagating yeast and/or conditioning yeast for fermentation. Oftentimes, such vessels are a fraction of the size of fermentation vessels. For example, such vessels can have a volumetric capacity in the range from about 1,000 US gallons to about 75,000 US gallons, or from about 10,000 US gallons to about 30,000 US gallons.

As shown in FIG. 2, a source of slurry 115 is in fluid communication with tank 220 via line 216 so that tank 220 can be filled with the slurry to a desirable level for propagation and/or conditioning.

Also, as shown in FIG. 2, yeast source 210 is in fluid communication with tank 220 so that yeast can be combined with slurry 115 and form an aqueous composition that can be subjected to conditions for yeast propagation and/or yeast conditioning.

Propagating yeast is generally well known and involves providing conditions to allow yeast to reproduce to provide a larger cell mass of yeast. Propagating yeast is typically performed by a yeast supplier or a yeast purchaser. In the context of a yeast purchaser, oftentimes the purchaser will buy an amount of yeast and then propagate the yeast themselves so as to obtain a larger, more desirable, cell mass of yeast in a more cost effective manner. Exemplary methods of propagating yeast are described in U.S. patent application having Ser. No. 13/798,617 and filing date Mar. 13, 2013 (Narendranath), wherein the entirety of said application is incorporated herein by reference for all purposes.

In some embodiments, conditions for yeast conditioning are the same as conditions for yeast propagation, although yeast propagation typically involves aerating the propagation medium to maintain the dissolved oxygen level at or above the minimum needed for effective yeast propagation. As described herein, an "aerated yeast propagation" reactor can provide a level of oxygen to the propagation medium of at least 1 volume of air per volume of medium (vvm), preferably at least 0.5 vvm of air. Yeast conditioning typically does not involve aerating the conditioning medium, especially in the context of using corn mash slurries as the conditioning medium because such slurries can be challenging to aerate due to their viscosity and presence of particulate material.

After conditioning and/or propagation in tank 220, a volume of the aqueous composition from the tank 220 can be removed and pitched to first fermentation reactor 120 via line 225. In some embodiments, the entire volume in tank 220 is transferred (i.e., pitched) to reactor 120. The volume of the aqueous composition that is pitched from tank 220 to reactor 120 can serve as an inoculum for fermentation in reactor 120. Exemplary volumes of aqueous compositions that can be pitched from tank 220 to reactor 120 include volumes from 5,000 US gallons to less than 100,000 US gallons. In some embodiments, the volume of aqueous compositions that can be pitched from tank 220 to reactor 120 includes a volume from 10,000 US gallons to 40,000 US gallons (e.g., 20,000 US gallons).

After or while the volume of aqueous composition is pitched from tank 220 to fermentation reactor 120, reactor 120 can be filled with slurry 115 via lines 117 and 116 to a form an aqueous composition that can be fermented in reactor 120. According to an aspect of the present invention, a volume of the aqueous composition in the first fermentation reactor 120 can be pitched to a second fermentation reactor 130 via line 125 in a similar manner as described above with respect to FIG. 1. The volume of the aqueous composition that is pitched from reactor 120 to reactor 130 can serve as an inoculum for fermentation in reactor 130.

After yeast is pitched to a fermentation reactor such as reactors 120, 130, and 140, fermentation can be performed as desired according to any desired fermentation protocol. Fermentation is well-known.

After fermentation, alcohol can be recovered from the fermented beer via, e.g., distillation. Distillation is also well-known.

Exemplary methods of fermentation and distillation are described in U.S. Pat. No. 7,842,484 (Lewis), wherein the entirety of said patent is incorporated herein by reference for all purposes.

Example 1—Pitching Yeast Continuously from One Fermentor to Another Fermentor

Example 1 demonstrates that yeast can be pitched continuously from one fermentor to another fermentor in series as similarly described above with respect to FIG. 1. Example 1 was conducted in laboratory scale in raw starch (BPX™) fermentation (i.e., a process that does not "cook" starch prior to fermentation).

Corn flour ground to 95% fines (i.e. >95% of the particles pass through a 0.5 micron sieve) was mixed with backset from a BPX biorefinery to yield a slurry with 35% total solids. The experiment was performed in triplicate. Three 100 mL fermentor bottles were used with 60 mL slurry per bottle. After mixing the corn flour with backset separately in each fermentor bottle, the slurry in each bottle was pH adjusted to 4.5 using dilute sulfuric acid or 45% w/w potassium hydroxide. Then, lactoside 247 for prevention of bacterial contamination and urea for nitrogen source to yeast were added at 2.5 ppm and 4 mM, respectively. A raw starch enzyme blend was added at a dose equivalent to 221 L per 550,000 gal fermentor to hydrolyze the starch and form glucose. Then, yeast (*Saccharomyces cerevisiae*) was inoculated at 0.33 g (dry)/L. The yeast was a genetically modified yeast that expresses glucoamylase and is commercially available under the tradename TransFerm® from Mascoma Corporation. After inoculation of the yeast, the fermentor bottles were conditioned in a water bath at 31.1° C. (88° F.). Samples were withdrawn at 24, 48, 72, and 88 h after yeast inoculation and analyzed for ethanol, glucose, glycerol, and organic acids using high performance liquid chromatography (HPLC). The 88 h samples were also analyzed for residual starch content. At 24 h, a portion (~3.2 g) from each of the 3 reactors was transferred to a fresh set of 3 reactors with similar corn mash and additives. This is similar to adding yeast from a yeast prop or conditioning tank in an ethanol producing biorefinery. Then, the $2^{nd}$ set of 3 reactors was also placed in the water bath at 88° F. (31.1° C.) for 88 h. Sampling and analysis of these reactors were similar to the first set. After 24 h of inoculation of the second set of reactors, 3.2 g from each reactor were transferred to a third set of reactors. Such cycles were repeated for about 15 consecutive cycles of continuously pitching the yeast from one set of reactors to the other every 24 h. A control set of 3 reactors was included. The control set had yeast inoculated to them from 8 h old yeast conditioning tanks Samples were also withdrawn from the control set of reactors at 24, 48, 72, and 88 h after yeast inoculation from the yeast conditioning tanks Samples were analyzed for ethanol, glucose, glycerol, and organic acids. The 88 h samples were also analyzed for residual starch.

Figure 3:
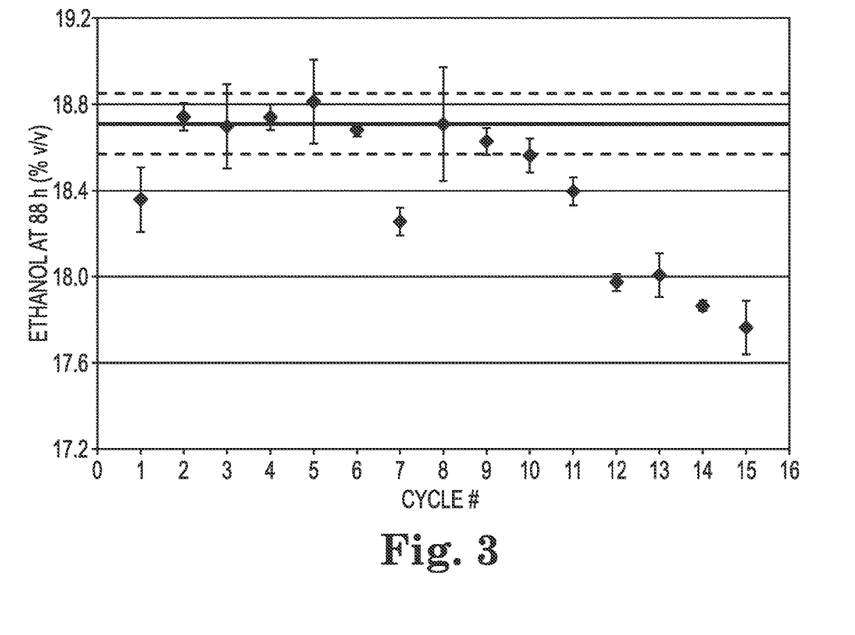
FIG. 3 shows a graph of ethanol concentration at 88 hours for each cycle (i.e., each fermentation reactor) in Example 1.
Figure 4:
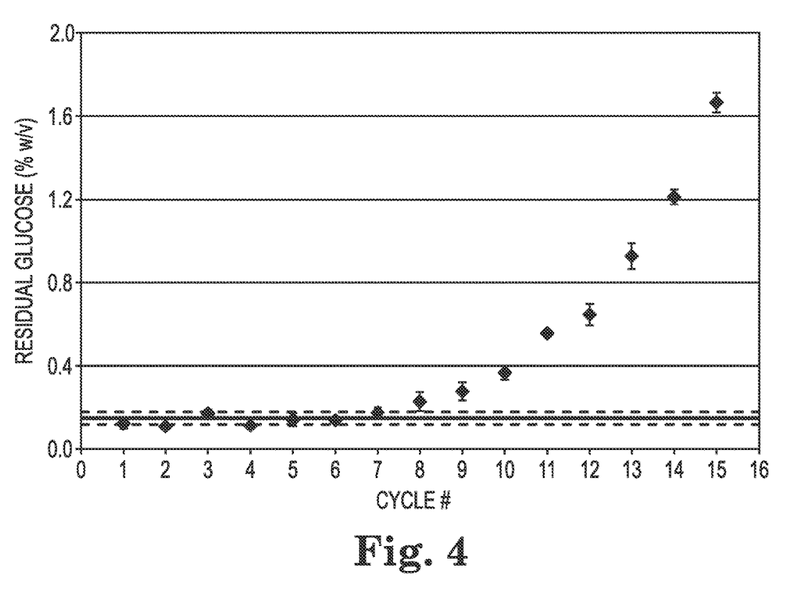
FIG. 4 shows a graph of residual glucose for each cycle in Example 1.
Figure 5:
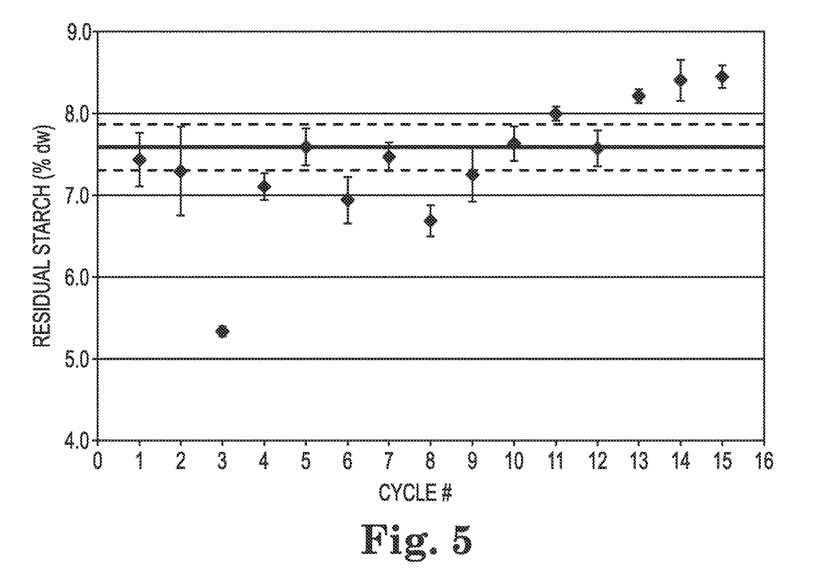
FIG. 5 shows a graph of residual starch for each cycle in Example 1.
Figure 6:
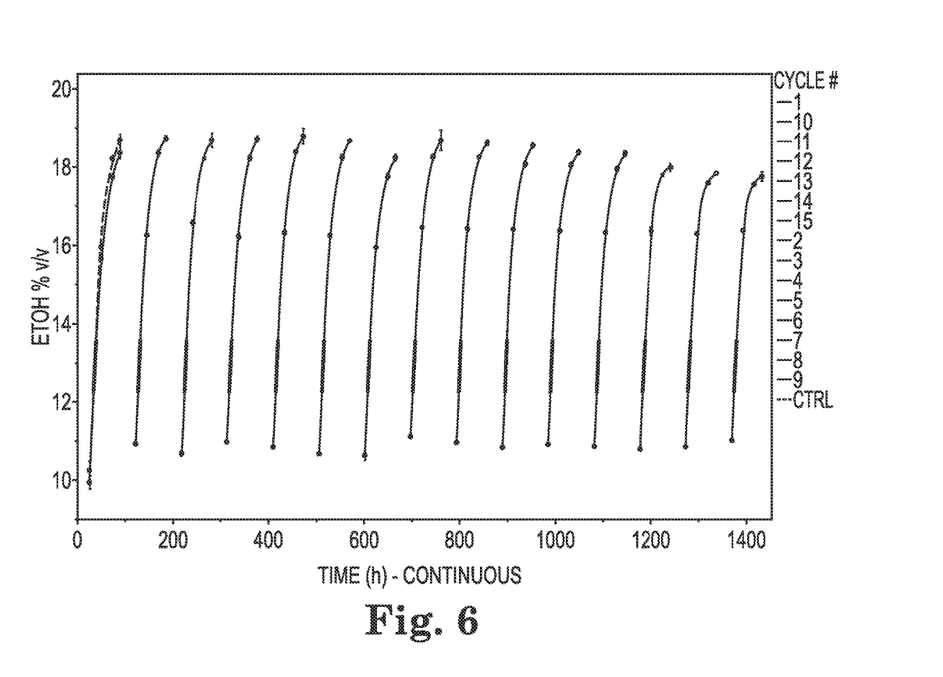
FIG. 6 shows a graph of ethanol production rate for each cycle in Example 1.

The results showed that such continuous yeast pitching from one fermentor to another fermentor can be successfully carried out for at least 7 consecutive cycles as evidenced by the ethanol titers achieved, residual glucose and residual starch present after each fermentation cycle (FIGS. 3, 4, and 5). FIG. 3 is a graph showing the ethanol produced after each cycle. The error bars for each data point indicate ± Standard Deviation from the mean of triplicate fermentations. The thick solid line indicates the average ethanol produced by the control fermentors and the dotted lines indicate the range (± Standard Deviation). FIG. 4 is a graph showing the residual glucose after each cycle. The error bars for each data point indicate ± Standard Deviation from the mean of triplicate fermentations. The thick solid line indicates the average ethanol produced by the control fermentors and the dotted lines indicate the range (± Standard Deviation). FIG. 5 is a graph showing the residual starch after each cycle. The error bars for each data point indicate ± Standard Deviation from the mean of triplicate fermentations. The thick solid line indicates the average ethanol produced by the control fermentors and the dotted lines indicate the range (± Standard Deviation). Additionally, no major differences were observed in the rates of ethanol production rate during each cycle (FIG. 6) which is indicative of no major changes in yeast populations from one cycle to another. The error bars for each data point indicate ± Standard Deviation from the mean of triplicate fermentations. The black dotted line indicates the rate of ethanol production in the control fermentors. Moreover, the rate of ethanol production observed in each fermentation cycle was similar to that of the control. Such a process of continuously pitching yeast from one fermentor to another fermentor may significantly reduce the yeast cost for any ethanol biorefinery.

Example 2

Figure 7:
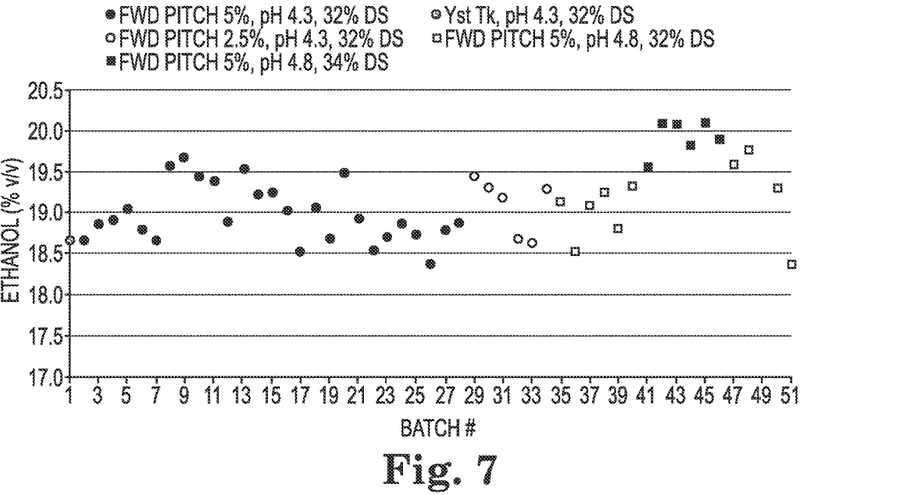
FIG. 7 shows a graph of the ethanol production in Example 2.
Figure 8:
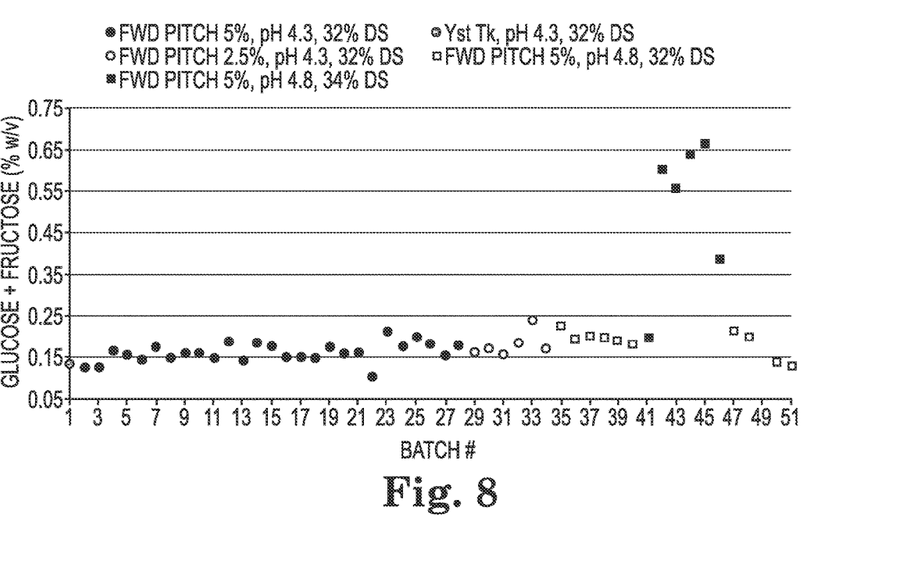
FIG. 8 shows a graph of the residual sugars (glucose+fructose) in Example 2.
Figure 9:
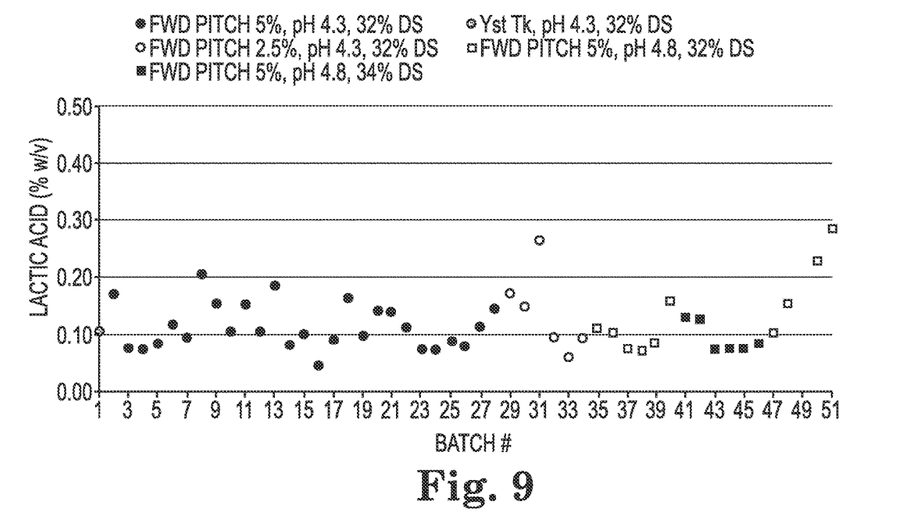
FIG. 9 shows a graph of the lactic acid in the fermentors in Example 2.
Figure 10:
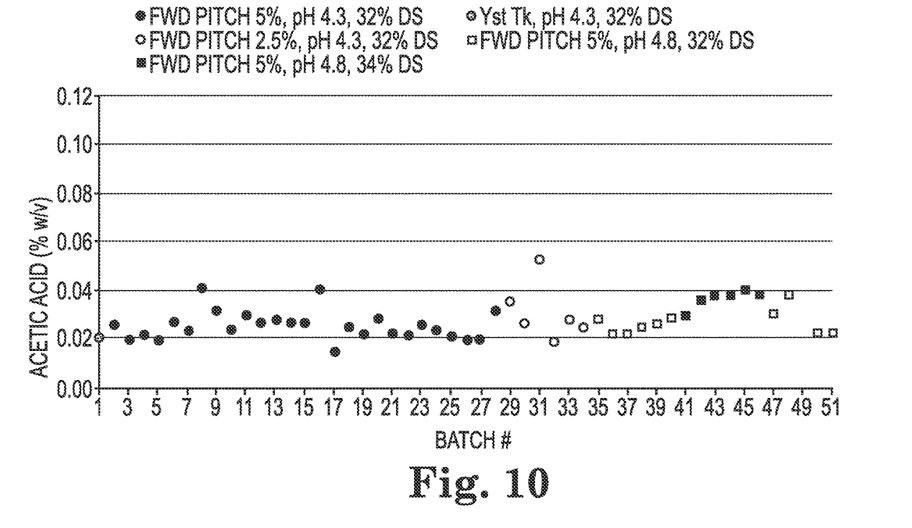
FIG. 10 shows a graph of the acetic acid produced in Example 2.

Example 2 was conducted at pilot scale facility in 20,000 gal fermentors. In the pilot plant, corn flour was mixed with backset and other process waters to make up a slurry at 32-34% fill solids. A raw starch enzyme blend, BPX10.5C, was added to the slurry at the required dose that would provide 0.32 AGU (alpha glucosidase unit) s/g dry solids and 0.03 FAU-F (fungal alpha amylase unit) s/g dry solids. The slurry (about 800 gal), was pH adjusted to 4.3 and was fed to a yeast prop/conditioning tank to which lactoside 247™ was added at 2-5 ppm and urea added at ~300 ppm. The same slurry also was used to fill the fermentor tanks Ethanol Red® active dry yeast was used during this trial. The fermentor initially was pitched with yeast grown/conditioned in the yeast conditioning tank for 10-12 hours. After 16 h, about 5% of the volume of the fermentor was transferred to the next fermentor. This 5% serves as the conditioned yeast inoculum in the second fermentor. The process was then continued from the second to the third fermentor and so on so that a series of batch fermentors can effectively operate continuously because yeast was pitched after successive 16 hour time blocks from the most recently "pitched to" fermentor to a new fermentor to start a new fermentation process over a total time period where a batch fermentation process is always in process. While the batch fermentors were continuously pitched with content from the previous fermentor at 16 hours of conditioning, a few variations were tested such as increasing the pH of the slurry, reducing the transfer volume from 5% to 2.5%, and increasing the fill solids. This operation was continued successfully in the pilot plant for over 50 fermentors with yeast from one single initial yeast conditioning tank. Such an operation can eliminate any variations caused due to conditioning yeast for each batch and also quite significantly reduce the fresh yeast usage. It is also likely that the yeast strain eventually may be adapted to the specific process. The results of ethanol produced after 78 h of fermentation, residual glucose, lactic and acetic acids from this trial are shown in FIGS. 7 through 10. FIG. 7 is a graph showing the ethanol produced in the fermentors pitched with yeast continually from one to the other starting originally from one yeast conditioning tank in batch 1. FIG. 8 is a graph showing the residual sugars (glucose+fructose) after 78 h in the fermentors pitched with yeast continually from one to the other starting originally from one yeast conditioning tank in batch 1. FIG. 9 is a graph showing lactic acid in the fermentors pitched with yeast continually from one to the other starting originally from one yeast conditioning tank in batch 1. FIG. 10 is a graph showing acetic acid produced in the fermentors pitched with yeast continually from one to the other starting originally from one yeast conditioning tank in batch 1.

The results in Example 2 from the pilot study confirms both the scalability and the resiliency of the continuous yeast pitching to a batch fermentation process for ethanol production in a dry grind facility.

Example 3

Figure 11:
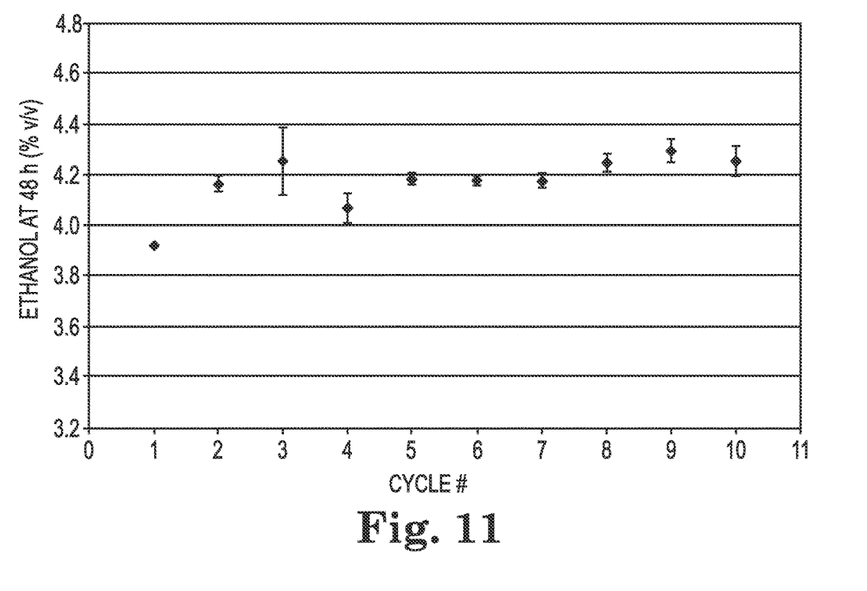
FIG. 11 shows a graph of the ethanol produced in Example 3.
Figure 12:
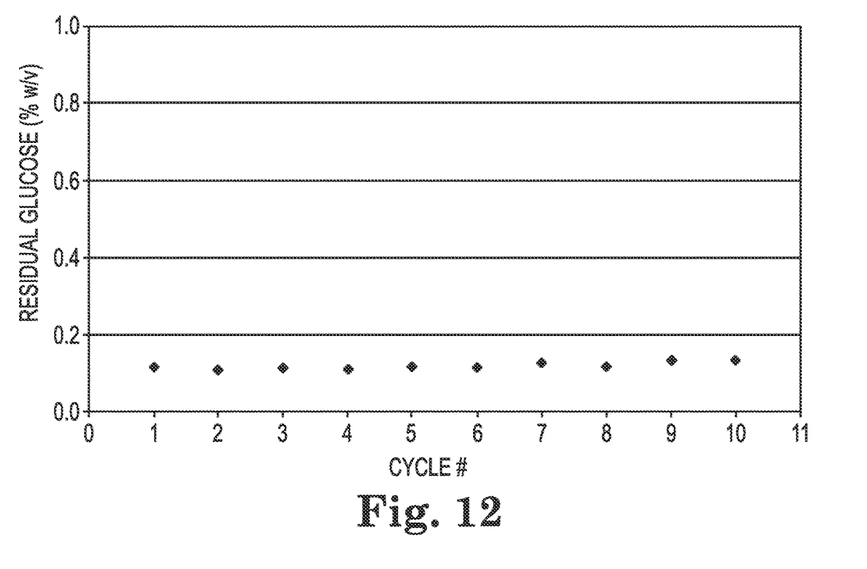
FIG. 12 shows a graph of the residual glucose in Example 3.
Figure 13:
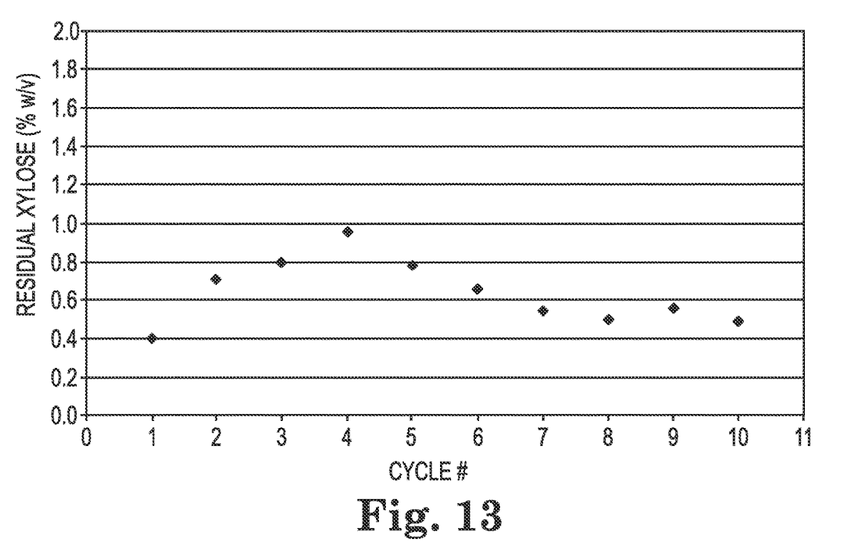
FIG. 13 shows a graph of the residual xylose in Example 3.
Figure 14:
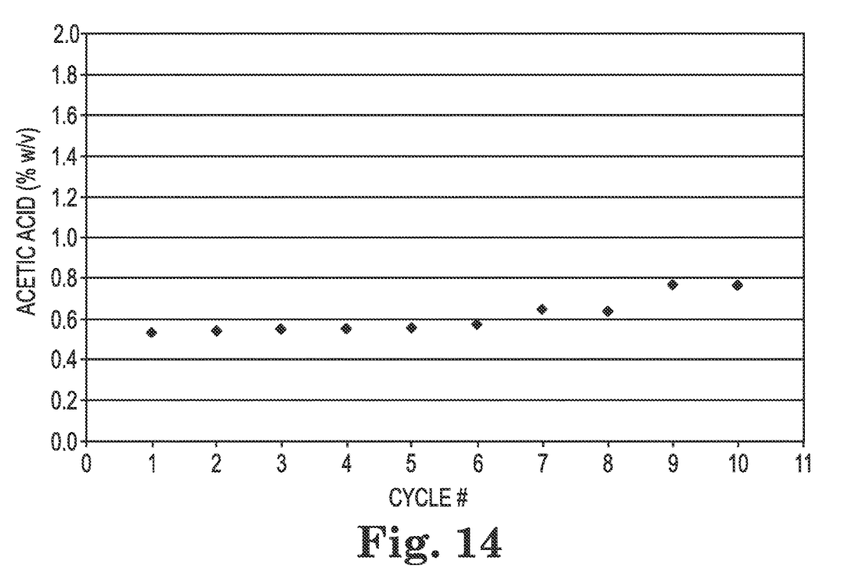
FIG. 14 shows a graph of acetic acid in the medium after each cycle in Example 3.

Example 3 demonstrates that genetically modified yeast capable of metabolizing xylose can successfully be pitched continuously from one fermentor to another in series. Dilute acid pretreated corn stover, pretreated at a pilot facility using 0.59% acid was used for this. Both C6 solids and C5 liquor from acid pretreatment were mixed to form a slurry of 17% solids, pH adjusted to 5.5, and saccharified at 50° C. using the appropriate cellulase mix (CTec3) for 120 h. After saccharification, the broth was stored at 4° C. Post saccharification, the glucose and xylose in the medium were measured at 4.81 and 4.13% w/v, respectively. The experiment was performed in duplicate. Two, 125 mL Erlenmeyer flasks were used with 50 mL of the saccharified broth per flask. After dispensing 50 mL of the broth to each flask, the pH of the material in each flask was adjusted to 5.5 using ammonium hydroxide. Then, lactoside 247™ was added at 5 ppm to each flask to prevent any bacterial contamination. Then, the genetically modified yeast grown on Yeast Extract, Peptone media supplemented with glucose (10 g/L) and xylose (20 g/L) was harvested, washed, and was inoculated to the flasks at 1 g (dry yeast)/L per flask. After inoculation of the yeast, the flasks were placed in a water bath shaker set at 32° C. (89.6° F.), and 150 rpm. Samples were withdrawn at 24, and 48 h after yeast inoculation and analyzed for ethanol, glucose, xylose, and acetic acid using high performance liquid chromatography. At 24 h, a portion (~5.0 g) from each of the 2 flasks was transferred to a fresh set of 2 flasks with 50 mL of the same saccharified broth adjusted to pH 5.5 using ammonium hydroxide. This would be similar to adding the yeast from a yeast propagation tank at a cellulosic ethanol production facility. Then, the second set of flasks were placed in the water bath at similar conditions. Such cycles were repeated for about 10 consecutive cycles of continuously pitching yeast from one set of flasks to the other every 24 h. The results of ethanol produced after 48 h, residual sugars and acetic acid from the study are shown in FIGS. 11 through 14. FIG. 11 is a graph showing ethanol produced after each cycle in a continuous yeast pitch type of fermentation in a lignocellulosic biomass to ethanol process. The error bars indicate ± Standard Deviation from the mean of duplicate fermentations. FIG. 12 is a graph showing residual glucose after each cycle in a continuous yeast pitch type of fermentation in a lignocellulosic biomass to ethanol process. The error bars indicate ± Standard Deviation from the mean of duplicate fermentations. FIG. 13 is a graph showing residual xylose after each cycle in a continuous yeast pitch type of fermentation in a lignocellulosic biomass to ethanol process. The error bars indicate ± Standard Deviation from the mean of duplicate fermentations. FIG. 14 is a graph showing acetic acid in the medium after each cycle in a continuous yeast pitch type of fermentation in a lignocellulosic biomass to ethanol process. The error bars indicate ± Standard Deviation from the mean of duplicate fermentations.

The results in Example 3 showed that the continuous yeast pitching from one fermentor to another fermentor can be successfully carried out for at least up to 10 cycles even in the lignocellulosic biomass to ethanol process. In the cycles where the residual xylose appeared to go up over 0.5% w/v, this can be reduced by increasing fermentation time by an additional 12-24 h.

What is claimed is:

1. A method of pitching yeast for fermentation, the method comprising:
providing a first aqueous composition in a first fermentation reactor, wherein the first aqueous composition comprises:
yeast;
a slurry comprising water and a processed plant material comprising an amount of at least one monosaccharide; wherein the processed plant material comprises corn flour and the slurry further comprises one or more enzymes that can break down starch in the corn flour into glucose;
fermenting the first aqueous composition in the first fermentation reactor to form a first beer composition comprising alcohol;
providing a fraction of the first beer composition to a second fermentation reactor, wherein the first beer composition in the first fermentation reactor comprises an alcohol at a concentration of at least 15 percent by volume when the fraction of the first beer composition is removed from the first fermentation reactor, and wherein the fraction of the first beer composition comprises a fraction of the yeast and the alcohol;
combining a slurry with the fraction of the first beer composition in the second fermentation reactor to form a second aqueous composition in the second fermentation reactor, wherein the slurry comprises water and a processed plant material comprising an amount of at least one monosaccharide; wherein the processed plant material comprises corn flour and the slurry further comprises one or more enzymes that can break down starch in the corn flour into glucose; and distilling the first beer composition from the first fermentation reactor to recover alcohol.

2. The method of claim 1, wherein adding the yeast to the first fermentation reactor comprises dry-batching yeast to the first fermentation reactor.

3. The method of claim 1, wherein, prior to removing the fraction of the first beer composition from the first fermentation reactor, at least the fraction of the first aqueous composition is exposed to a temperature in the range from 15° C. to 50° C. for a time period in the range from 5 to 30 hours.

4. The method of claim 1, wherein the fraction of the first beer composition is removed from the first fermentation reactor after the first fermentation reactor is filled with the first aqueous composition.

5. The method of claim 1, wherein the first beer composition in the first fermentation reactor further comprises an alcohol at a concentration of at least 19 percent by volume when the fraction of the first beer composition is removed from the first fermentation reactor.

6. The method of claim 1, wherein the corn flour is provided from a dry corn milling process.

7. The method of claim 1, further comprising,
fermenting the second aqueous composition in the second fermentation reactor to form a second beer composition comprising alcohol;
removing a fraction of the second beer composition from the second fermentation reactor to a third fermentation reactor;
continuing to ferment the second aqueous composition in the second fermentation reactor after the removing the second beer composition; and
distilling the second beer composition from the second fermentation reactor to recover alcohol.

8. The method of claim 1, further comprising, prior to providing the first beer composition in the first fermentation reactor:
providing an initial pitching aqueous composition in a yeast conditioning reactor and/or an aerobic yeast propagation reactor, wherein the initial pitching aqueous composition comprises:
yeast;
a slurry comprising water and a processed plant material comprising an amount of at least one monosaccharide; wherein the processed plant material comprises corn flour and the slurry further comprises one or more enzymes that can break down starch in the corn flour into glucose; and
removing the initial pitching aqueous composition from the yeast conditioning reactor and/or aerobic yeast propagation reactor to form the first aqueous composition that is provided to the first fermentation reactor.

9. The method of claim 8, wherein, prior to removing the initial pitching aqueous composition from the yeast conditioning reactor and/or aerobic yeast propagation reactor, the initial pitching aqueous composition in the yeast conditioning reactor and/or aerobic yeast propagation reactor is exposed to a temperature in the range from 15° C. to 50° C. for a time period in the range from 5 to 30 hours.

10. The method of claim 8, wherein the yeast conditioning reactor and/or the aerobic yeast propagation reactor has a capacity of less than 100,000 gallons and the first and second fermentation reactors each have a capacity greater than 100,000 gallons.

11. The method of claim 1, wherein the fraction of the first beer composition from the first fermentation reactor has a volume in the range from 10,000 gallons to 40,000 gallons and the first aqueous composition that is fermented in the first fermentation reactor has a volume in the range from 100,000 gallons to 750,000 gallons.

12. The method of claim 1, wherein the fraction of the first beer composition is from 1.3% by volume to 13.3% by volume based on the total volume of the first aqueous composition.

13. The method of claim 1, wherein fermenting the first aqueous composition in the first fermentation reactor occurs for a total time period in the range from 25 to 150 hours.

14. A method of pitching yeast for fermentation, the method comprising:
providing a first aqueous composition in a first fermentation reactor, wherein the first aqueous composition comprises:
yeast;
corn flour;
a slurry comprising water and one or more enzymes that can break down starch in the corn flour into one or more monosaccharides;
fermenting the first aqueous composition in the first fermentation reactor to form a beer composition comprising alcohol;
providing a fraction of the beer composition to a second fermentation reactor, wherein the fraction of the beer composition comprises a fraction of the yeast and the alcohol and wherein the fraction of the beer composition is removed from the first fermentation reactor from 8 hours to 24 hours after the first aqueous composition is provided in the first fermentation reactor; wherein the first fermentation reactor comprises an alcohol at a concentration of at least 15 percent by volume when the fraction of the beer composition is removed from the first fermentation reactor;
combining a slurry with the fraction of the beer composition in the second fermentation reactor to form a second aqueous composition, wherein the second aqueous composition comprises:
corn flour; and
a slurry comprises water and one or more enzymes that can break down starch in the corn flour into one or more monosaccharides; and
distilling the beer composition from the first fermentation reactor to recover alcohol.

15. A method of pitching yeast for fermentation, the method comprising:
(a) providing a first aqueous composition in a first batch fermentation reactor, wherein the first aqueous composition comprises:
yeast;
a slurry comprising water and a processed plant material comprising an amount of at least one monosaccharide; wherein the processed plant material comprises corn flour and the slurry further comprises one or more enzymes that can break down starch in the corn flour into glucose;
(b) fermenting the first aqueous composition in the first batch fermentation reactor to form a first beer composition comprising alcohol;
(c) providing a fraction of the first beer composition to a second batch fermentation reactor; wherein the first batch fermentation reactor comprises an alcohol at a concentration of at least 15 percent by volume when the fraction of the beer composition is removed from the first batch fermentation reactor to the second batch fermentation reactor; and wherein the fraction of the first beer composition comprises a fraction of the alcohol and the yeast;
- (d) continuing to ferment the first aqueous composition in the first batch fermentation reactor after removing the fraction of the first beer composition;
- (e) combining a slurry with the fraction of the first beer composition in the second batch fermentation reactor to form a second aqueous composition in the second batch fermentation reactor, wherein the slurry comprises water and a processed plant material comprising an amount of at least one monosaccharide; wherein the processed plant material comprises corn flour and the slurry further comprises one or more enzymes that can break down starch in the corn flour into glucose;
- (f) fermenting the second aqueous composition in the second batch fermentation reactor to form a second beer composition comprising alcohol; and
- (g) providing a fraction of the second beer composition to a third batch fermentation reactor when the second beer composition comprises alcohol, wherein the fraction of the second beer composition comprises a fraction of the alcohol and the yeast;
- (h) continuing to ferment the second aqueous composition in the second batch fermentation reactor after removing the fraction of the second beer composition; and
- (i) distilling beer from each of the first and second batch fermentation reactors.

16. The method of claim 15, wherein steps (e)-(i) are repeated at least 4 times in four additional batch fermentation reactors.

\* \* \* \* \*